United States Patent [19]

Elmeskog

[11] 4,333,340

[45] Jun. 8, 1982

[54] DEVICE FOR MEASUREMENT OF MUSCULAR STRENGTH

[76] Inventor: Alf U. Elmeskog, Minkvägen 13, S-754 60 Uppsala, Sweden

[21] Appl. No.: 132,842

[22] PCT Filed: Jul. 24, 1979

[86] PCT No.: PCT/SE79/00161
 § 371 Date: Mar. 25, 1980
 § 102(e) Date: Mar. 24, 1980

[87] PCT Pub. No.: WO80/00308
 PCT Pub. Date: Mar. 6, 1980

[30] Foreign Application Priority Data

Jul. 25, 1978 [SE] Sweden .............................. 7808119

[51] Int. Cl.³ .............................................. G01L 5/02
[52] U.S. Cl. ...................................................... 73/379
[58] Field of Search ...................................... 73/379

[56] References Cited

U.S. PATENT DOCUMENTS

| | | | |
|---|---|---|---|
| 3,103,357 | 9/1963 | Berne | 73/379 |
| 3,285,070 | 11/1966 | McDonough | 73/379 |
| 3,323,366 | 6/1967 | Lorme, Jr. et al. | 73/379 |
| 3,465,592 | 9/1969 | Perrine | 73/379 |

FOREIGN PATENT DOCUMENTS 2021130  9/1971  Fed. Rep. of Germany ........ 73/379

Primary Examiner—Donald O. Woodiel
Attorney, Agent, or Firm—Bacon & Thomas

[57] ABSTRACT

A bench device to be used for static or dynamic measurement of muscular forces with suitable opposing force providing means. The device comprises in combination a bunk (2) vertically adjustable on a base (1) and at least one holder (39) for a static or dynamic opposing force providing means (4) displaceably arranged at said base (1), said holder (39) and bunk (2) being steplessly adjustable in relation to each other both vertically and in the transverse and longitudinal directions of the bunk (2). Hereby it is possible to make various muscular force measurements on both sitting and lying persons.

5 Claims, 9 Drawing Figures

DEVICE FOR MEASUREMENT OF MUSCULAR STRENGTH

The present invention relates to a device for use in measuring and exercising muscular strength.

Measurement of muscular strength has recently got an increasingly extended use particularly in medical service, where it is used to follow up rehabilitation training as well as to determine the extent or degree of temporary or permanent injuries of various muscles or muscle groups. Also in athletic practice there are similar training devices, where predetermined values of the force to be resisted by the working muscles can be accurately adjusted.

The loading of the muscles in such muscular strength measurement or exercise is applied either statically or dynamically. In the static case the muscular force is exerted against a relatively immovable object. In this case the muscle in question does not move after its initial contraction, a so-called isometric contraction.

In the dynamic case the muscle or muscles in question have to overcome an opposing force during a whole muscular movement. Such a force may for example be provided by weights or springs, but particularly advantageous in this connection are devices permitting isokinetic contraction, i.e. a contraction having a constant speed of the muscular movement over the full range of movement, the applied resisting force varying with the magnitude of the muscular force. Thus, in measuring muscular force with such a device the variation of the muscular force in the different parts of the range of movement may be recorded for different speeds, the muscular force not being uniform throughout the entire range of motion. Physiologically the muscle is strongest when fully extended, while mechanically the body part controlled by the muscle can exert the greatest force in the midrange due to the anatomic levers. In addition the muscular force in a certain position may be impeded by for example experience of pain. Thus, isokinetic measurement of muscular power give considerably more information about the state of the muscles of a person than static measurement of muscular strength.

A device giving such an isokinetic force is disclosed in e.g. U.S. Pat. No. 3,465,592. Said device has a lever, the fixed end of which is connected to the shaft of a force giver, while its free end is intended to be actuated by for example the arm or leg of the person whose muscular force is to be tested. For measurement of for example leg and thigh muscles there are for instance special chairs where the measuring device is secured by screws to one side or the other depending on which leg that is to be studied. For measurement of certain arm movements a bench has correspondingly been used where the person performs these arm motions lying. Therefore, it has up to now been relatively troublesome, inconvenient and time-consuming to shift between different measurements.

It is an object of the present invention to provide a measuring/exercising table for static and dynamic force givers, which table in a quick and simple way can be rearranged between different measuring positions for different types of muscular force measurements. The new measuring/exercising table can be used for measuring/exercising on persons in a sitting as well as a lying position without inconvenient dismounting and removal of the force giver between the different measurements. Through the invention it is thus possible to perform several different measurements and exercising moments respectively with one and the same measuring/exercising table. This is of great value particularly within medical service, since it considerably increases the examination capacity. Furthermore, the measuring/exercising table according to the invention permits such muscular measurements and exercise moments respectively that it previously has not been possible to perform for practical reasons. These together with other objects are achieved according to the invention with a measuring/exercising table having the features given in the subsequent claims.

A preferred embodiment of the invention will be described more in detail hereinafter, reference being made to the accompanying drawings, in which FIG. 1 is a perspective oblique front view of a measuring/exercising table according to the invention in a lowered position;

Figure 1:
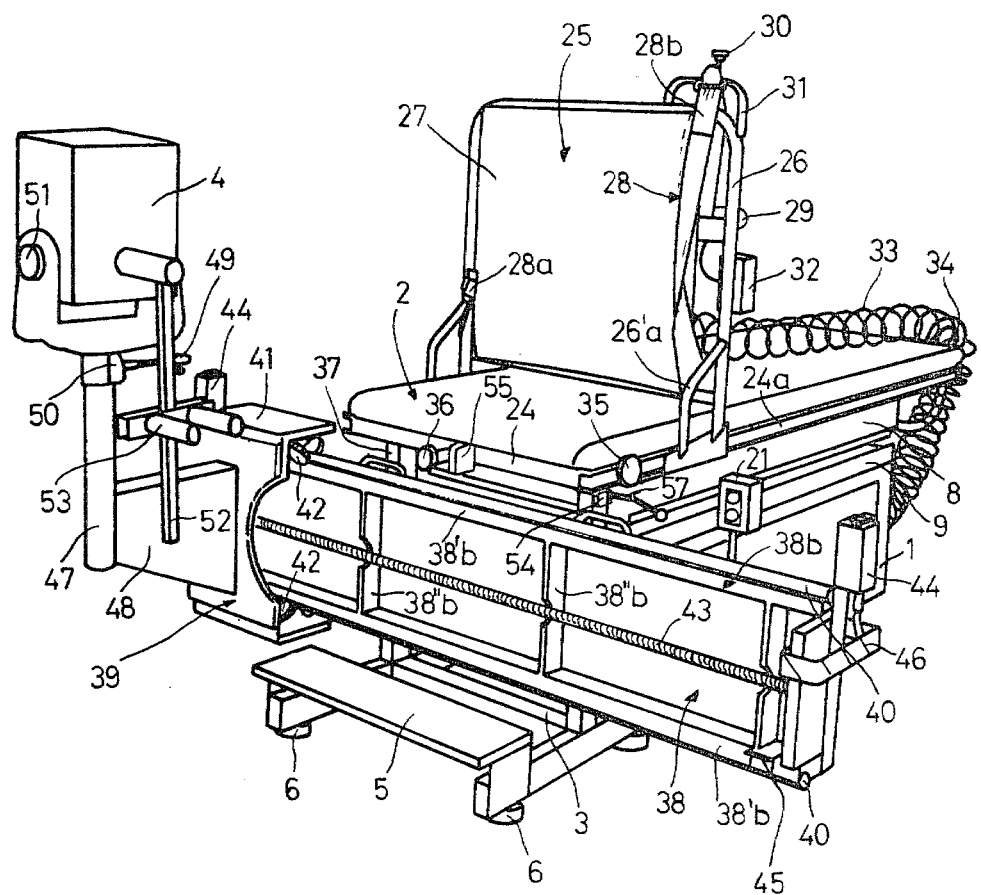
Figure 2:
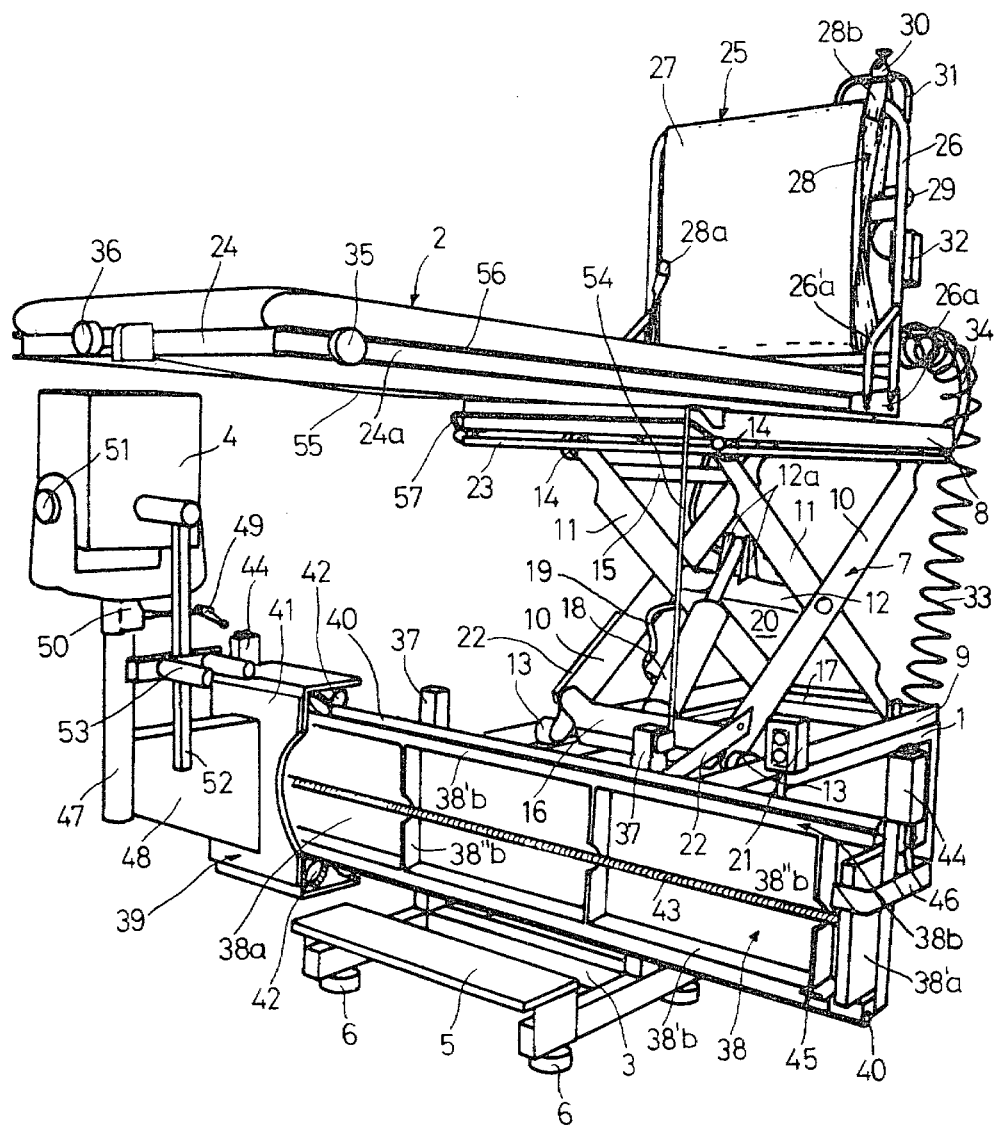
FIG. 2 is the same view as in FIG. 1 showing the measuring/exercising table in an elevated position.

The device shown in FIGS. 1 and 2 comprises a base 1 supporting a vertically adjustable bunk 2 provided with a back rest, and a holder 39 for an arbitrary force giver 4 for static or dynamic measurement or exercise of muscular strength, which holder is displaceable along a guiding construction 38 arranged at the front end of said base 1.

The base 1 consists in the shown case of a parallelepipedical frame construction whose lower frame portion is extended at the front end 3 to support a foot plate 5. The base 1 rests on suitably located so-called machine feet 6 of a conventional type.

An elevating device 7 in the form of a so-called lifting table for said bunk 2 is arranged on the base 1. Said lifting table comprises upper and lower frames 8 and 9, which are interconnected by a pair of scissors arms 10 and 11 at each long side. The arms 10 and 11 of each pair of scissors arms are pivotally connected with each other about a shaft 12 through their respective central portions. One arm 10 is at one end pivotally attached to a rear part of the upper frame 8, while its other end is displaceably arranged along the long side of the lower frame 9 through a wheel 13 fixed to the arm 10 and running in a rail on the inside of the lower part of the lower frame 9. Correspondingly the other arm 11 is at one end pivotally attached to the lower frame 9, while its other end is displaceably arranged along the long side of the upper frame 8 through a wheel 14 running in a rail on the inside of said upper frame 8. The two pairs of scissors arms are interconnected by means of the above mentioned shaft 12 as well as by cross bars 15, 16 and 17. A hydraulic piston/cylinder assembly 18 is disposed between the cross bar 16 and the shaft 12 to actuate said scissors arms 10, 11 to displace the frames 8 and 9 in relation to each other, the cylinder part being pivotally fixed to the bar 16 and the piston rod being pivotally fixed to the shaft 12 in two brackets 12a attached thereto. The piston/cylinder assembly is operated via a conduit 19 by for example a (not shown) hydraulic assembly with an electric motor, a pump and an oil tank on the back of a plate 20 between the two scissors arms 11. The elevating device 7 is controlled by control means 21 having knobs for switching it on and off. Said control means 21 are in turn connected to a (not shown) suitably located main circuit-breaker (corresponding control means 21 may be arranged on the other side of the table). In order to prevent the lifting table 7 from collapsing in case of e.g. a hose failure, the scissors arms 10 are in their lower parts provided with mechanical stops in the form of bar members 22 pivotally attached at one end so that the free end can be made to rest against the fore side edge of the lower frame 9. The bar members 22 can also be used to set the lifting table at a level predetermined by the length of said bar members. In addition a safety frame 23 for preventing pinching accidents is suspended just below the upper frame 8. Said safety frame is arranged to disconnect the current to the hydraulic assembly via a number of contact breakers at the lower edge of the upper frame 8 when the safety frame 23 is pressed against the frame 8.

The bunk 2 is displaceable on the upper frame 8 of the lifting table 7 in the longitudinal direction of the frame 8. The bunk 2 comprises a frame portion 24 to which a suitable, conventional bed pad or the like is fastened. The long sides of said frame portion 24 comprise outer guide rails 24a for displacement of a back rest 25 along the bunk 2 and inner guide rails (not shown) for stationary sliding and/or roller means on the (possibly covered) top of the upper frame 8. Suitably each one of the long sides 24a consists of a pair of channel bars arranged with their base portions against each other and their legs directed outwards and inwards respectively. The above mentioned stationary means at the top of the upper frame 8 can for example consist of angle bars located at each end of the long sides, said angle bars carrying a horizontal cross shaft on which one or possibly more travelling wheels are mounted in bearings. Said travelling wheels are adapted to roll in the above channel shaped guide rails when the bunk 2 is moved along the upper frame 8. Spacing means, e.g. two per side, are suitably arranged at each long side of the upper frame 8 to prevent lateral movement of the bunk 2 across said travelling wheels. Said spacing means may for example consist of blocks of a suitable material, e.g. Teflon ®. In order to lock the bunk 2 in a desired position along the upper frame 8, said parts are provided with suitable locking means. The latter may e.g. be a rod disposed in the frame portion 24 of the bunk 2 and in the longitudinal direction thereof. Said rod runs through recesses or holes in two disc or plate members placed after each other at the top of the upper frame 8. The disc or plate members are pivotally fixed at their base portion and spring biased, so that they in the normal or locked position are inclined in relation to the vertical line, the side edges of said holes bearing against said rod and preventing longitudinal movement thereof. To disengage the locking means, actuating means which can bring said disc or plate members to a substantially vertical position, e.g. a line or a wire, are connected to control means 57 therefore on the upper frame 8.

The back rest 25 comprises a frame or body 26 having a back portion 27 of a suitable, per se conventional type fixed thereto. The base portion of said back rest frame 26 is on each side of the bunk 2 provided with brackets 26a for suitable sliding means, e.g. blocks of Teflon ® or the like, which are arranged to slide in the outer channel-shaped guide rail 24a of the upper frame 8 when the back rest 25 is displaced along the bunk 2. To allow the back rest 25 to be fixed in a desired, arbitrary position along the bunk 2 locking means are disposed in said frame base portion of the back rest 25. These may for example be an element fixed to said back rest frame 26 above one of the guide rails 24a (or possibly both), which element can be made to expand downwards to contact the horizontal upper part of said guide rail 24a. The back rest is then displaced upwards in relation to the bunk 2, the above sliding blocks consequently being pressed against the upper part of the guide rail 24a so that the back rest 25 is fixed in this position. The locking means may also be of the electromagnetic type.

The back rest 25 is suitably provided with a fastening device 28 for the person to be examined or exercised. In the case shown said fastening device consists of a three-points so-called inertia safety belt of the type used in motor vehicles. The latter has a stationary belt part 28a on one side of the back rest 25, and a belt part 28b which can be wound on a reeling device 29 on the other side. From said reeling device 29 in the mid-portion of the frame 26 the extensible belt portion 28b runs through a bracket 30, which—to adapt the belt to persons of different sizes—can be laterally moved and fixed in an arbitrary position along a holder arm 31, to a fixing point in the lower part of the frame 26. The fastening belt 28 is preferably controlled electromagnetically via a control device 32. In the switched on position the belt 28b can then be pulled out of the reeling device 29 but in the switched off position only be wound onto the reeling device. Power is supplied to the control device via a helical cable 33 from a transformer and a distributor unit (not shown) on the backside of the base 1. In order that the cable 33 should not get pinched between the upper frame 8 and the guide rails 24a it is wound around a guide arm 34 at the back of the upper frame 8. The reference numeral 35 indicates a handle which in the shown case also functions as an end stop for the displacement of the back rest 25 along the bunk 2. The bunk 2 may also be arranged for fixing an extension part thereto, e.g. by a fastening means 36.

A guiding construction 38, along which a holder 39 for the force giver 4 can be moved, is fixed to the front corner posts 37 of the base 1 in the cross-direction thereof. Said guiding construction 38—which in order to provide the necessary stability in the shown case is designed as a guiding box formed by a box construction 38a having interior reinforcement elements and a frame work 38b arranged on the front thereof—protrudes outside the base 1 and permits continuous movement of the holder 39 between two end positions on either side of the bunk 2. The frame 38b comprises upper and lower horizontal frame members 38'b which support guide rods 40 on their upper side and underside respectively. The horizontal frame members are connected to vertical frame members 38"b. The holder 39 comprises a sliding carriage 41 which at the top and bottom is displaceably journalled in bearings on said guide rods 40 by means of roller bearings 42, e.g. double V-shaped roller chain guides. The movement of the sliding carriage 41 along the guiding box 40 is effected by means of an electric motor at the (not shown) end of the guiding box 38. The motor drives, via a transmission and a clutch, a threaded rod 43 mounted along the front of the guiding box 38 and rotatably journalled in bearings in gabels 38'a of the guiding box 38. The threaded rod 43 engages a stationary nut element on the inside of the sliding carriage 39. Said motor is switched on and off by means of control means 44 at the ends of the guiding box 38. The frame work 38b is suitably provided with limit switches 45 at its ends to automatically switch off the driving unit when the sliding carriage 41 reaches these positions. For safety's sake also (not shown) mechanical stops are arranged at the respective end portions. The sliding carriage 41 may of course also be manually displaceable along the guiding box 38. In that case the sliding carriage 41 is provided with a locking device with the aid of which it may be locked against the guiding box 38. At its two ends the guiding box 38 is equipped with safety frames 46. The holder 39 is provided with a fastening device for the force giver 4, e.g. a plate, (in the Figures hidden by the force giver 4), to which the force giver 4 may for example be secured by screws. The fastening device is rotatably arranged in the horizontal plane on a vertical support member 47 fixed to a bracket 48 protruding from the sliding carriage 41, and it can be fixed in a desired position by means of a locking device 50 actuated by a control arm 49. A protractor is suitably placed between said fastening device and the locking device 50 to permit reproducible angular setting of the force giver in relation to the support member 47. The force giver 4, which can be an isokinetic one of the type described in U.S. Pat. No. 3,465,592, is in the shown design rotatably arranged round a horizontal shaft 51 and provided with a lever 52 to be actuated by the extremity whose muscular force is to be determined or increased. The lever 52 is therefor provided with suitable fixing means 53 for the extremity in question.

For reproducible adjustment of the level of the bunk 2 above the floor the measuring and exercising table is provided with a suitable measuring device therefore, e.g. a measure tape 54 between the base 1 and the upper frame 8. For reproducible setting of the level of the bunk 2 in relation to the upper frame 8 for example a measure tape 55 is disposed at the underside of the frame portion 24. In the same way e.g. the upper side of one of the guide rails 24a is provided with a graduated portion or the like 56 for reproducible setting of the position of the back rest 25 along the bunk 2. Furthermore similar (not shown) measuring means are arranged for reproducible adjustment of the sliding carriage 41.

All the electric control means are connected to the (not shown) power supply connection, including a main circuit-breaker, a transformer and a distributing unit, of the measuring and exercising table.

Figure 5:
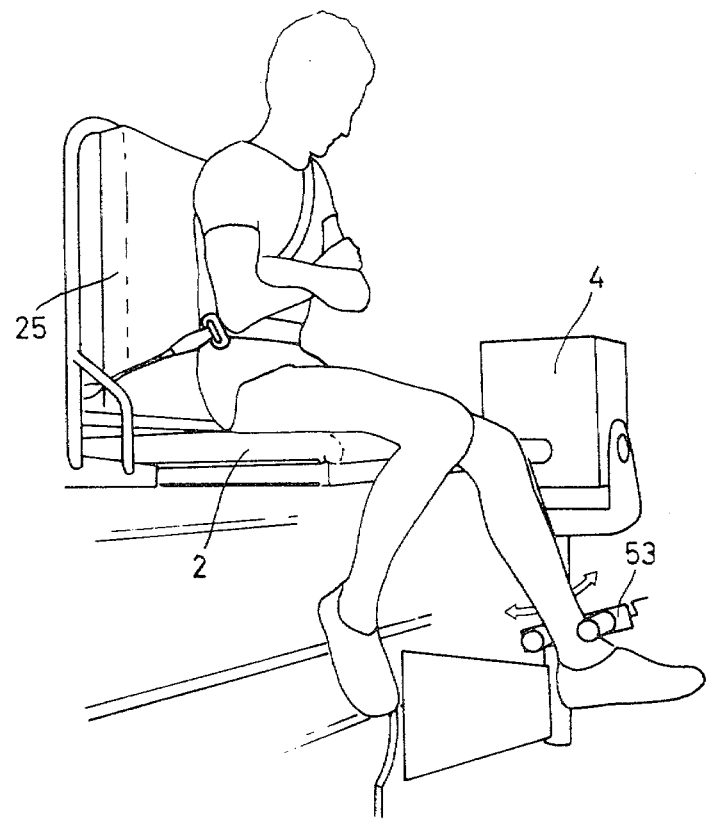

The operation of the above described measuring and exercising table is exemplified by determination of the muscular force when bending and stretching the knee respectively according to FIG. 5 using an isokinetic force giver:

First the force giver 4 is moved to the proper side by displacement of the sliding carriage 41 along the guiding construction or box 38. This is done by switching on the driving motor for rotation of the threaded rod 43 by means of either of the control means 44. The nut element on the inside of the sliding carriage 41—and consequently the sliding carriage 41—is then caused to move along the threaded rod 43, the double roller chain guides 42 at the top and bottom of the sliding carriage 41 sliding against the guide rods 40 on the horizontal frame members 38'b. The sliding carriage is stopped in a desired position by switching off the driving motor. When necessary the fastening device for the force giver 4 is turned so that the latter gets the proper position on the support member 47 after releasing the locking device 50 by the handle 49.

The bunk 2 is adjusted in relation to the upper frame 8 so that the front edge gets a suitable position in relation to the force giver 4. This is done by displacing the bunk 2 manually along the upper frame 8 of the lifting table 7. To make it possible to move the bunk 2 the above mentioned locking means acting between the bunk 2 and the upper frame 8 must be released. This is effected by turning the handles 57 to make the spring biased locking discs of said locking means stand vertically, said locking discs having holes and being disposed on the upper frame 8. The locking bar at the underside of the bunk 2 can then run freely through said holes. When the handles 57 are released the above mentioned locking discs, thanks to the spring bias, take the original oblique position preventing further motion of the locking bar in the holes of the locking discs.

The person to be examined is placed in a sitting position on the front end of the bunk 2, suitably when it is in the lowered position shown in FIG. 1. If necessary, further horizontal adjustment of the bunk 2 as above is performed. Then the back rest 25 is put in a suitable position along the bunk 2 so that the person in question can swing his legs freely. Removal of the back rest is done by disengaging said not shown locking means at the lower part of the back rest frame 26 which act against the upper side of the guide rail 24a, and manually removing the back rest to a desired position, the sliding blocks in the holder 26a sliding in the guide rail 24a. The back rest 25 is then fixed in this position by locking said locking means. The person in question is then secured with the fastening belt 28 after the bracket 30 has been adjusted to the proper position on the holder frame 31. When the electromagnetic control device 32 is switched on the belt portion 28b can be pulled out of the reeling device 29 and be coupled to the belt portion 28a on the other side of the back rest. After switching off the control device 32 the person in question is properly fastened which prevents the person from e.g. huddling when performing the leg movement to be studied and thereby detrimentally effecting the test result.

The bunk 2 is then adjusted to a suitable level with regard to the force giver 4 by means of the lifting table 7 which is operated by the control means 21. On elevation the piston rod of the piston/cylinder assembly 18 is pressed out of the cylinder part. Through this extension of the piston/cylinder assembly 18 the movable ends of the scissors arms 10 and 11 provided with travelling wheels 13 and 14 respectively are forced to be displaced against the rear end of the lower and upper frames 9 and 8 respectively so that the upper frame 8 of the lifting table is raised. By turning down the bar member 22 against the lower frame guide rail 9 for the travelling wheel 13 a collapse of the lifting table through e.g. a leak of a hydraulic conduit is prevented.

If necessary the position of the sliding carriage 41 is then fineadjusted as above. The position of the fixing means 53 on the lever 52 is adjusted according to the length of the legs of the sitting person, and the very measurement is carried out by letting the person in question actuate the lever 52 by his leg in the direction of the arrows in FIG. 5. The isokinetic force giver 4 then gives a loading force which is automatically adjusted so that the speed of the leg is constant throughout the motion. Said loading force is recorded on a recorder or a corresponding device for evaluation. The various set values of the measure tapes 54, 55 and 56 and of the protractor on the fastening device of the force giver 4 are noted to make it possible to make exactly the same measurement on a later occasion.

As previously mentioned it is of great importance that the measuring and exercising table of the invention is stable, particularly the guiding box 38 and the holder 39 for the force giver 4 mounted thereon, so that all power delivered by the person in question is taken up by the force giver 4. Otherwise misleading measurement results are obtained, particularly at the beginning of the movement of the extremities, a so-called hysteresis effect.

Figure 3:
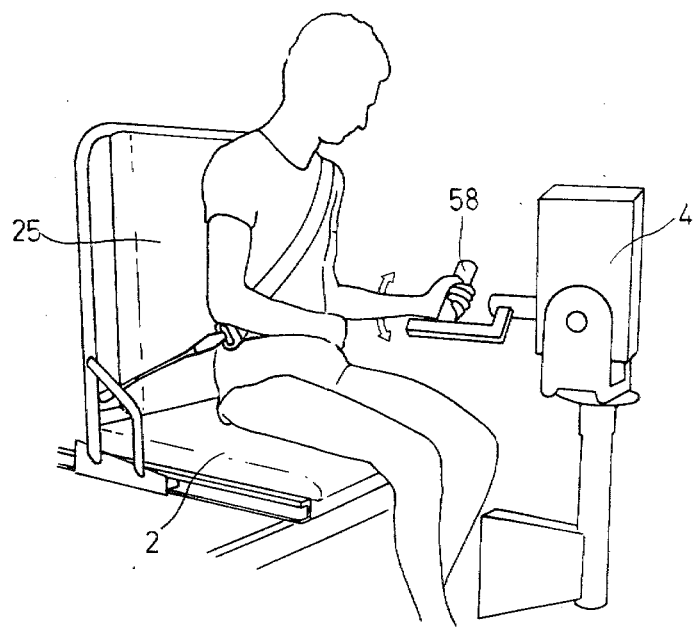
FIGS. 3–5 are schematic perspective views showing examples of different types of measurement/exercise of muscular strength which can be performed with the device according to the invention on a sitting person.

FIG. 3 shows measurement at pro-supination, i.e. turning of the hand in the direction of the arrows with the upper arm secured against the body, e.g. by a not shown holder for the elbow fixed to the back rest or by a band round the upper part of the body. The patient is fastened in a sitting position in the same way as for the above described measurement, the adjustment of the position of the bunk 2 vertically and horizontally respectively as well as of the back rest 25, the fastening belt 28 and the sliding carriage 41 being done as above. In this measurement the force giver 4 has, however, been turned 90° in the horizontal plane and the lever 52 been substituted by another lever 58 provided with a handle.

Figure 4:
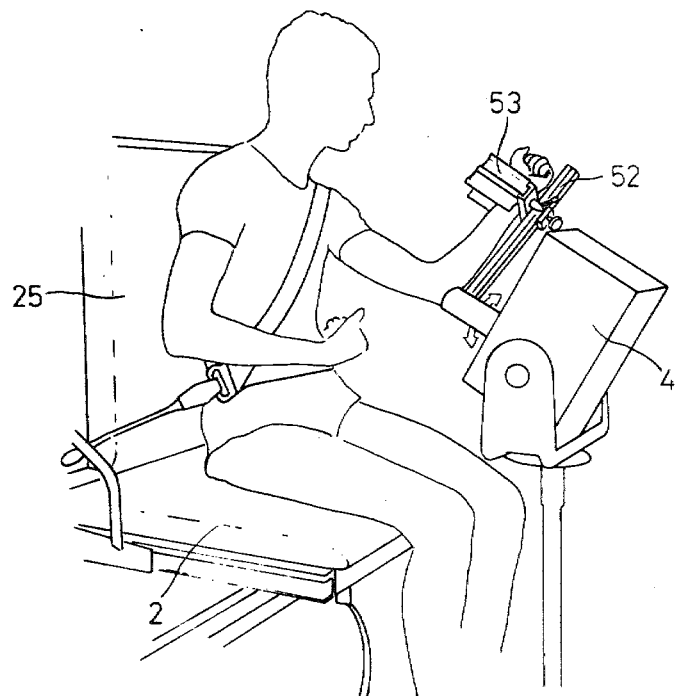

FIG. 4 shows a measurement at pro-supination as above but with the upper arm abducted and elevated about 45° with an elbow joint angle of about 90°. In this case the elbow shall in addition rest in a not shown support, e.g. a padded elbow holder fixed to the force giver 4. In this measurement the force giver 4 is inclined 45° towards the vertical line and the lever 52 in FIG. 2 substituted by a shorter one having a suitable fixing device 53.

Figure 6:
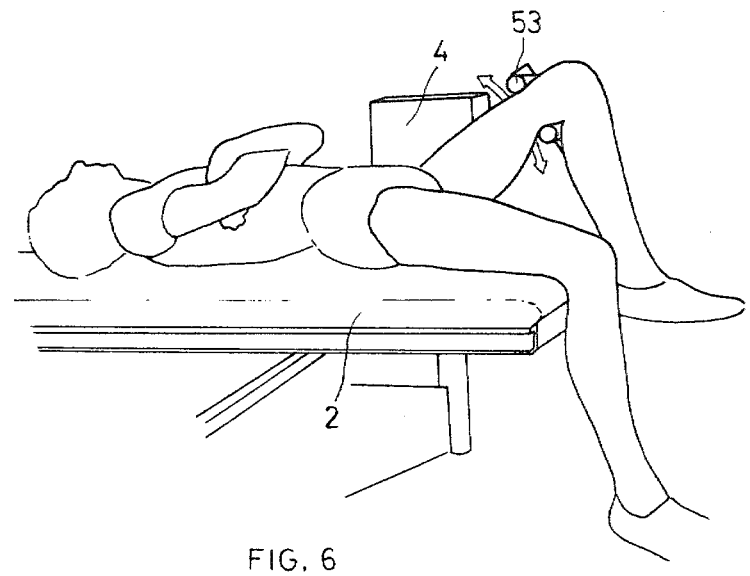
FIGS. 6–9 correspondingly show examples of different types of measurement/exercise of muscular strength on a lying person.

FIG. 6 shows a measurement at hip extension-hip flexion with a bent knee-joint. This measurement is performed with a lying patient, and the back rest 25 is therefore removed backwards on the bunk 2. The bunk 2 is set at a suitable level and pushed forward to permit the shown position of the patient in relation to the force giver 4. The patient then actuates the lever 52 in the direction of the arrows by means of the fixing device 53. The force giver 4 has the same position as in FIG. 5.

Figure 7:
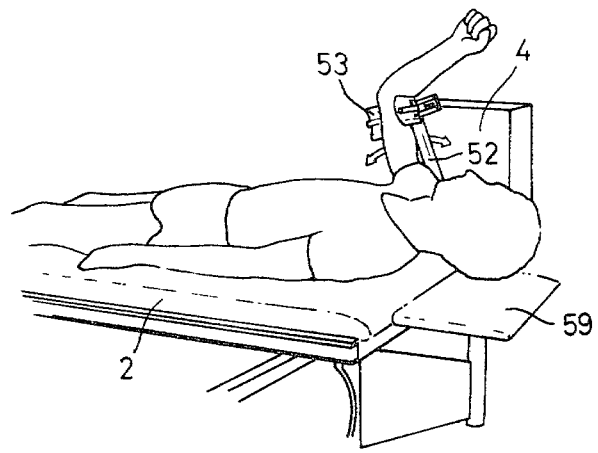

FIG. 7 shows a measurement on the upper arm at elevation forwards-upwards (flexion) and lowering of the arm (extension) with a bent elbow. Here the patient lies fully stretched out on the bunk 2 which has been extended by an extension piece 59 (for extremely tall persons) by means of the fastening means 36 of the bunk. The lever 52 of the force giver 4—which has the same position as in FIG. 6—is actuated in the direction of the arrows.

Figure 8:
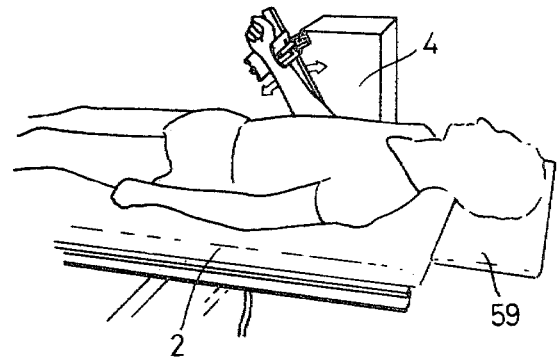

FIG. 8 shows a measurement on the upper arm at flexion-extension of the elbow-joint with the patient lying in the same way as in the measurement in FIG. 7. The lever 52 of the force giver 4 is actuated in the direction of the arrows.

Figure 9:
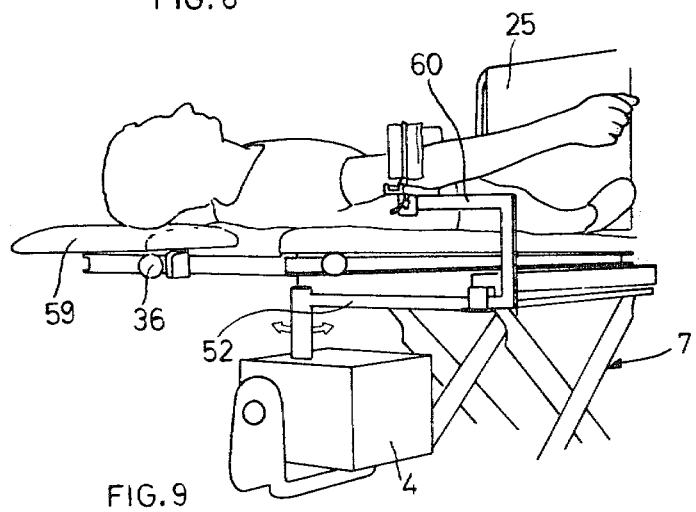

FIG. 9 finally shows a measurement on the forearm at abduction-adduction of the shoulder-joint. The patient lies in the same way as in FIGS. 7 and 8, but the force giver 4 is here rotated 90° round its shaft 51, so that the lever 52 is in the horizontal plane. The patient actuates it in the direction of the arrows via an L-shaped spacing piece 60, to which the fixing device 53 is attached.

The above described measurements are only examples of muscular force measurements which can be performed with the measuring and exercising table according to the invention. Muscular exercise with the new device is done analogously. As appears from the above the table can quickly and easily be readjusted for different measurements (and exercise moments respectively) on the same or different patients.

The invention is of course not restricted to the above specially described embodiment, but many variations and modifications are possible within the scope of the general inventive idea. Thus, instead of one holder 39 for the force giver 4 it is possible to use one on either side of the bunk 2. In the latter case the two holders 39 may be stationary and instead the bunk 2 may be displaceable in the transverse direction. A laterally displaceable bunk 2 may also be arranged in combination with one or two movable holders 39. It is also possible to dispose one or two holders 39 at either end of the base 1. The holder or holders 39 may be movable in the longitudinal direction of the bunk 2, in which case the bunk 2 need not be displaceable in its longitudinal direction. Instead of the described guiding construction 38 it is further possible to have a horizontal arm pivotally arranged at the base 1 and supporting the holder 39, or possibly one such arm on each side of the bunk 2. As to the guiding construction 38 it may be vertically adjustable in relation to the base 1, so that for e.g. a bunk level fixed by the bar members 22 the level of the force giver 4 may be adjusted in relation to the bunk. In the embodiment shown in FIGS. 1 and 2 the displacement of the back rest 25, which may be articulated, and of the bunk 2 in the longitudinal direction may of course be done by means of driving motors. Further, the different measure tapes etc. 54, 55, 56 may be substituted by other measuring means, e.g. electronic ones. The elevating device 7 may of course also be designed in different ways and may consist of other devices than hydraulic piston/cylinder assemblies.

I claim:

1. A bench device for measuring muscular forces with static or dynamic opposing force providing means, comprising a base, a bunk having a back-rest adjustable therealong, said bunk being vertically adjustable on said base and longitudinally displaceable therealong, guiding means arranged at one end of said base below the plane of said bunk and substantially perpendicular to the longitudinal direction of the bunk, and at least one holder for static or dynamic opposing force providing means, which is horizontally displaceable along said guiding means between end positions on either side of said bunk, said holder and bunk thus being continuously adjustable relative to each other vertically as well as transversely and longitudinally to the bunk to render various measurements of muscular forces possible on a sitting as well as a lying person.

2. A device according to claim 1, wherein said guiding means comprises an essentially box-shaped structural frame support.

3. A device according to claim 2, wherein said holder comprises a slide slidably mounted on said structural frame support along upper and lower guide means supported thereby.

4. A device according to claim 3, characterized in that said slide is arranged to be moved by means of a driving motor, which drives a threaded bar mounted in said structural frame support, said threaded bar engaging a nut member disposed in said slide.

5. A device according to claim 1, wherein the vertical adjustment of said bunk is effected by means of an elevating device placed between the bunk and the base and comprising a preferably hydraulically driven scissors arms means.

* * * * *